United States Patent [19]
Hogendijk et al.

[11] Patent Number: 5,713,907
[45] Date of Patent: Feb. 3, 1998

[54] APPARATUS AND METHOD FOR DILATING A LUMEN AND FOR INSERTING AN INTRALUMINAL GRAFT

[75] Inventors: Michael Hogendijk, Santa Clara, Calif.; Mark H. Wholey, Allegheny County, Pa.

[73] Assignee: Endotex Interventional Systems, Inc., Menlo Park, Calif.

[21] Appl. No.: 504,820

[22] Filed: Jul. 20, 1995

[51] Int. Cl.[6] ............................................. A61M 29/00
[52] U.S. Cl. ........................................ 606/108; 606/198
[58] Field of Search .............................. 606/198, 108; 604/105, 106, 107, 108

[56] References Cited

U.S. PATENT DOCUMENTS

| | | | |
|---|---|---|---|
| 1,433,031 | 10/1922 | Pegaitaz | 606/198 |
| 3,557,794 | 1/1971 | Van Patten | 606/198 |
| 3,667,474 | 6/1972 | Lapkin et al. | 606/198 |
| 3,874,388 | 4/1975 | King et al. | |
| 3,996,938 | 12/1976 | Clark | 606/198 X |
| 4,562,596 | 1/1986 | Kornberg | |
| 4,585,000 | 4/1986 | Hershenson | |
| 4,733,665 | 3/1988 | Palmaz | |
| 4,739,762 | 4/1988 | Palmaz | |
| 4,776,337 | 10/1988 | Palmaz | |
| 4,820,298 | 4/1989 | Leveen et al. | |
| 4,998,539 | 3/1991 | Delsanti | 606/198 |
| 5,002,560 | 3/1991 | Machold et al. | 606/198 |
| 5,151,105 | 9/1992 | Kwan-Gett | |
| 5,279,565 | 1/1994 | Klein et al. | 604/105 |
| 5,354,310 | 10/1994 | Garnic et al. | 606/198 |
| 5,456,667 | 10/1995 | Ham et al. | 606/198 X |

*Primary Examiner*—Michael H. Thaler
*Attorney, Agent, or Firm*—Fish & Neave

[57] ABSTRACT

An insertion device for an intraluminal graft is provided, including a deployment catheter which has a deployment shaft and an expanding frame with an umbrella-like assembly. The assembly is suitable for radially expanding a graft. The device also includes a deployment grip connected to the deployment shaft. A coil interposed between the deployment grip and the expanding frame resiliently urges the expanding frame, with the deployment grip reversibly operating the expanding frame thereby. The deployment catheter collapses for removal from the vessel lumen after the intraluminal graft has been introduced therein. This intraluminal graft is deployed through a catheter and expanded in place to anchor the graft to the vessel wall. The expanding frame is then collapsed and withdrawn from the lumen. The insertion device also can be configured as an intraluminal dilation device that can be used to dilate a lumen and to ensnare an intraluminal object.

18 Claims, 11 Drawing Sheets

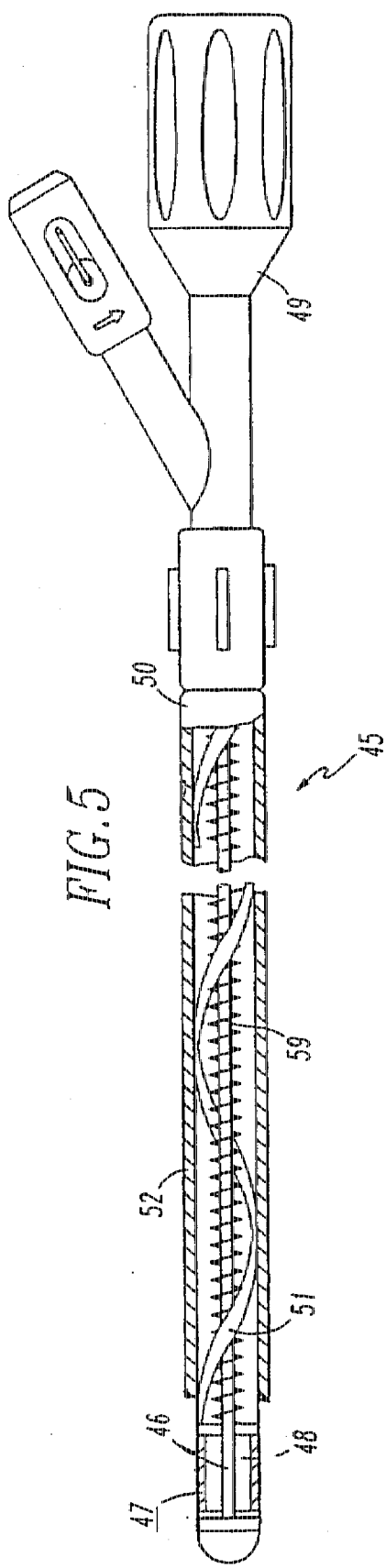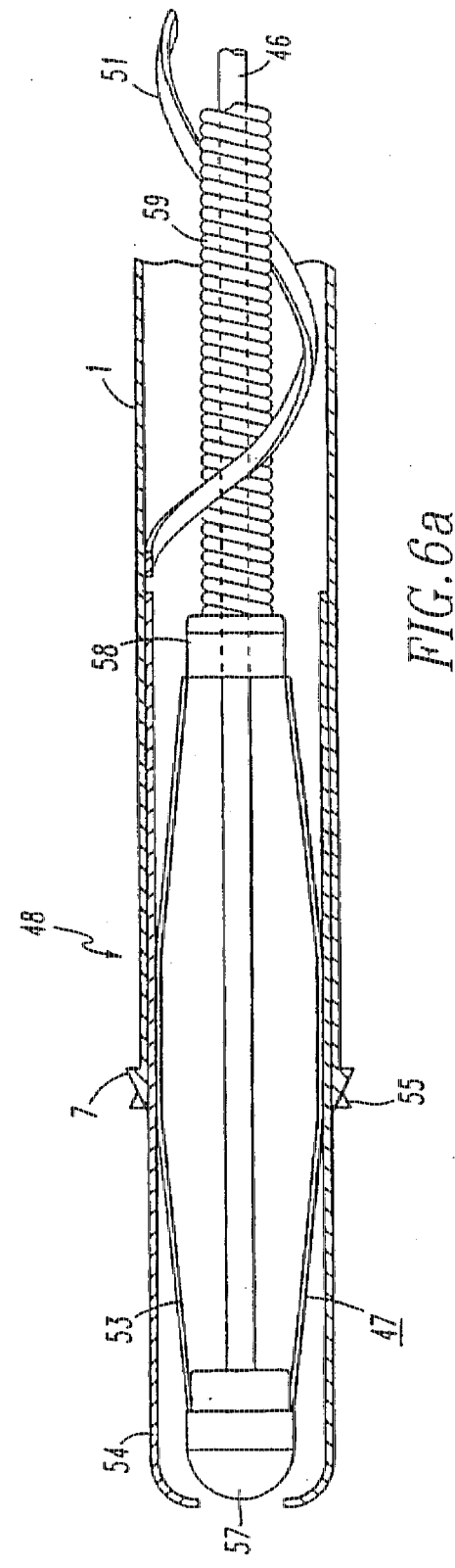

FIG. 7a
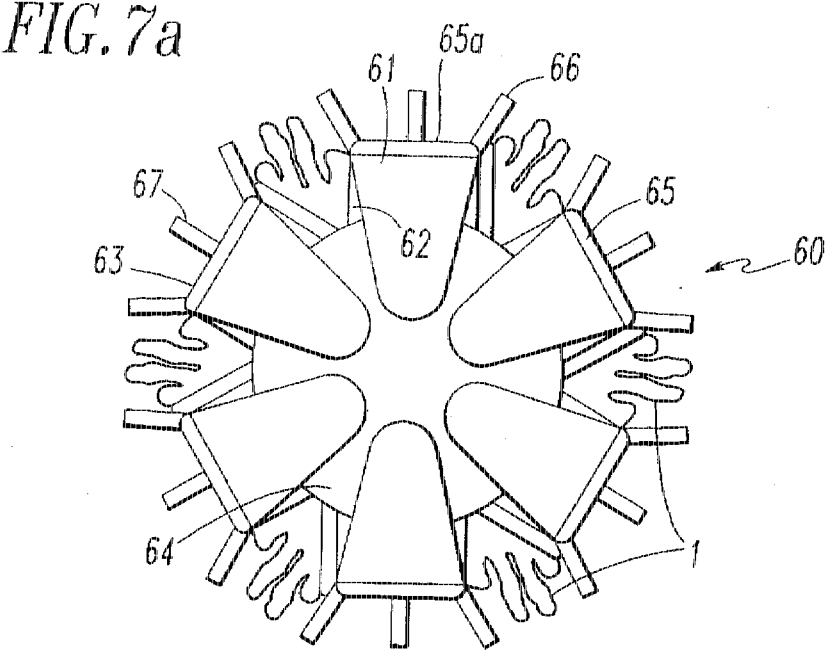
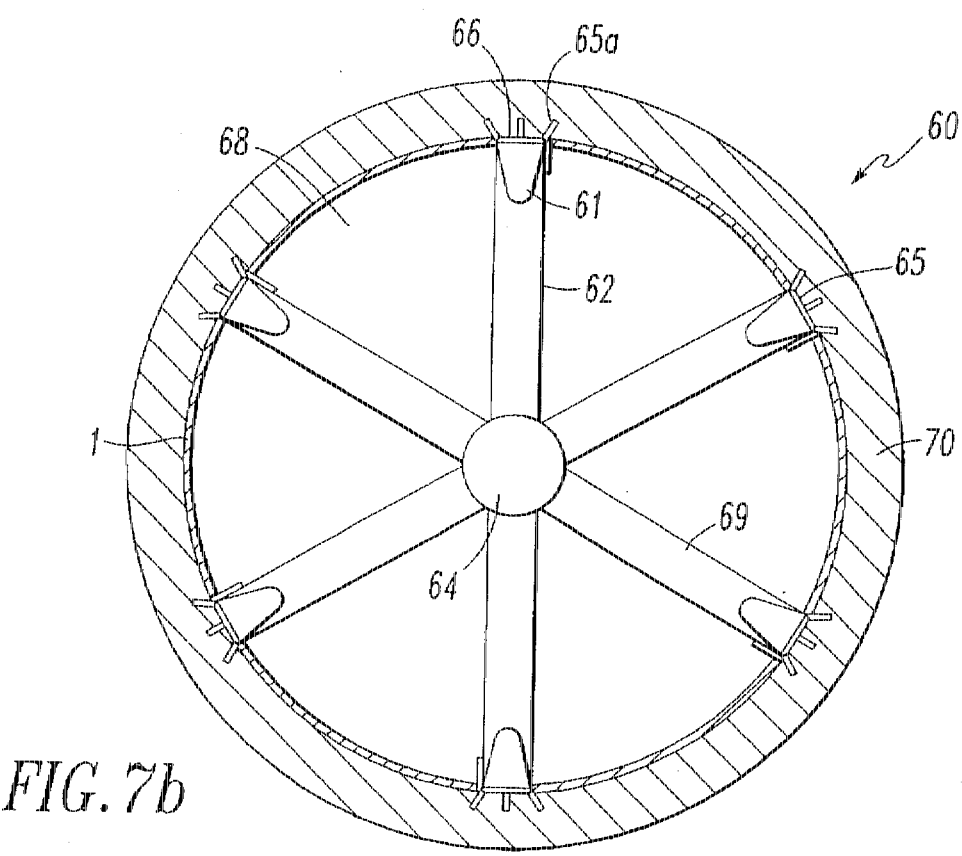
FIG. 7b

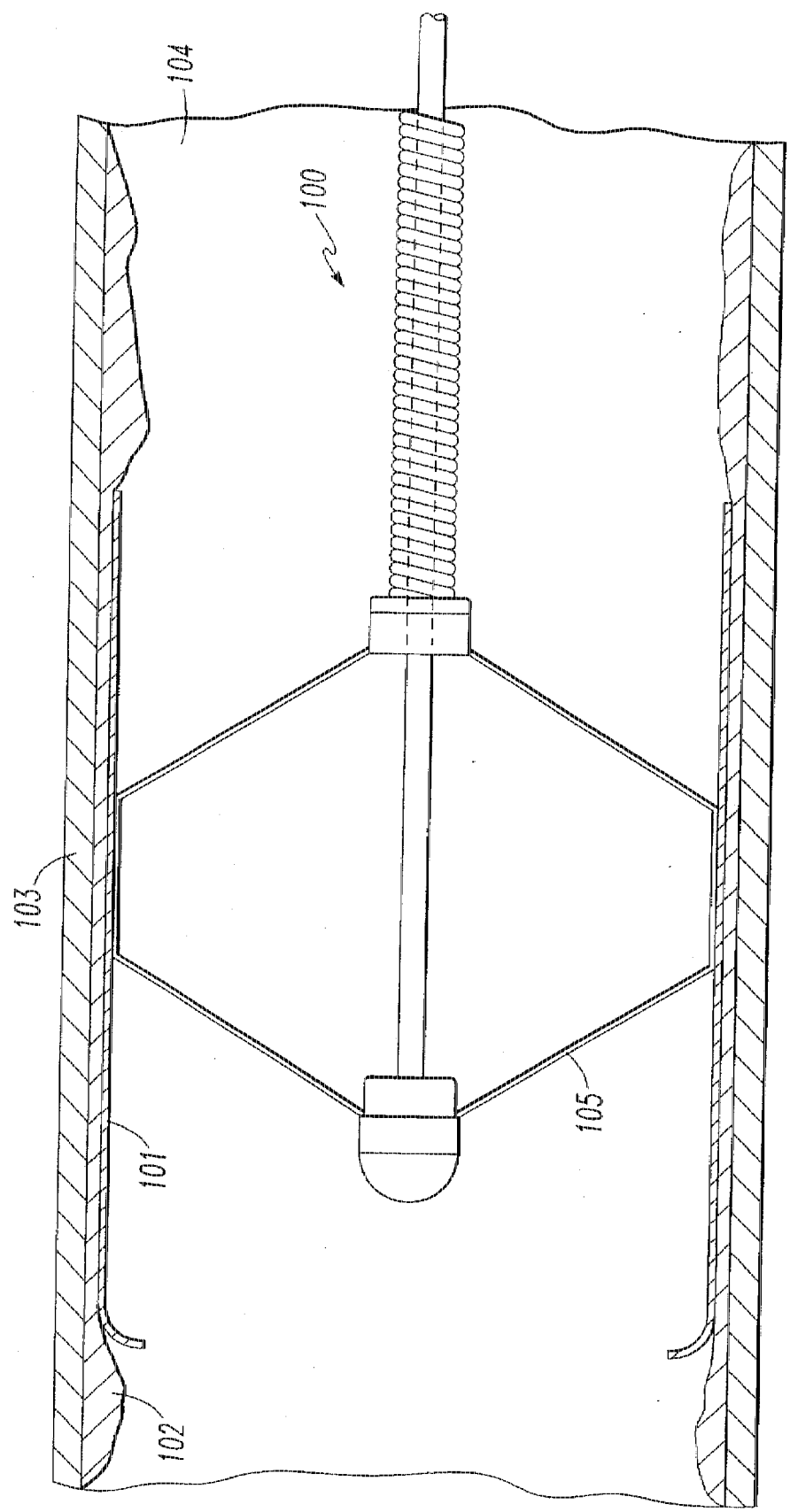

APPARATUS AND METHOD FOR DILATING A LUMEN AND FOR INSERTING AN INTRALUMINAL GRAFT

BACKGROUND OF THE INVENTION

1. Field of the Invention

This invention relates to insertion devices for implantable intraluminal grafts, or prostheses, and more particularly, to insertion devices that are removable once the graft is implanted into a body lumen or cavity and that may be used to dilate a lumen.

2. Description of the Prior Art

Surgical intervention for intracavitary or intraluminal defects often require highly-invasive surgical techniques. These techniques are typically performed under general anesthesia and can involve deep and extensive incisions into the tissues of the body to expose the affected parts, and provide the surgeon with adequate access thereto. As used herein, endoluminal defects includes both intraluminal and intracavitary defects. Also, endoluminal defects can include the dilation, narrowing, or occlusion of, or the accretion of foreign materials within a body lumen or cavity, and can affect many anatomical entities including those in the vascular, gastrointestinal, pulmonary, reproductive, genitourinary, and hepatobiliary systems.

One type of endoluminal defect is an aneurysm. An aneurysm can be defined as a localized, irreversible enlargement of an artery. Though aneurysms may develop at any point along the aorta, about eighty percent of them occur in the abdominal area. Of these, most develop below the renal arteries. In general, once an abdominal aortic aneurysm (AAA) develops, the dynamics of blood flow tend to promote its enlargement. Typically, the abdominal aorta averages between two and two-and-a-half centimeters in diameter. As the aneurysm grows, particularly beyond 5 centimeters, the likelihood of its rupture increases sharply. A ruptured aortic aneurysm is a catastrophic event. Over all, mortality from a ruptured AAA ranges from about fifty percent to over ninety percent. Even if the patient does survive, irreversible renal failure or loss of gastrointestinal function may result from organ ischemia related to hypotension. Similarly, paraplegia may occur from prolonged spinal cord ischemia and may be permanent.

However, not all aneurysms present an imminent threat of death or profound incapacitation. In general, aneurysms less than five centimeters in diameter have a low immediate risk of rupture and may be managed medically, typically through lifestyle changes and antihypertensive medication. But, an aneurysm that is five centimeters or larger, or becomes symptomatic, generally dictates surgical intervention.

Surgical repair of an AAA usually is performed under general anesthesia and involves replacing the aneurysmal segment of the aorta with a synthetic graft. To access the aneurysm, the surgeon must cut through skin, fat, and muscle, and then move the bowel out of the way. The sections of the aorta distal to the aneurysm often are clamped to reduce blood loss. The diseased portion of the aorta is excised and replaced with an implantable graft. After the graft is in place, the clamps are removed, the patients' intestines are returned to the abdominal cavity, and the multiple layers of tissue are sutured or stapled closed. Complications of such major surgery can include cardiac ischemia and arrest, pneumonia, kidney and bowel injury, paralysis, and infection.

In most cases, the patient is between 60 and 70 years old when an AAA is discovered. Often, the patient may have concurrent chronic health problems such as diabetes, heart disease, diminished pulmonary function, and the like. Surgery of this nature may not be a viable option for a significant number of patients with these coexisting problems.

As an alternative, intraluminal endovascular grafting has been developed to avoid the aforementioned extraordinarily invasive open-abdomen aneurysm repair procedures. Intraluminal grafting can involve the percutaneous insertion into a blood vessel of a tubular prosthetic graft and its delivery via a catheter to the desired location within the vascular system. The advantages of this method over conventional vascular surgery include obviating the need for surgically exposing, incising, removing, replacing, or bypassing the defective blood vessel, and reducing post-surgical complications.

One such intraluminal device is a collapsible vessel sleeve implant that may be placed in position within the aorta by a catheter and positioning wires via an incision, or cut-down, into the femoral artery, as in U.S. Pat. No. 5,151,105 (Kwan-Gett). This sleeve implant, or graft, employs concentrically wound lengths of thin, flat spring material, such as stainless spring steel, to provide the radial outward expansion of the ends of the graft against the interior wall of the vessel under repair. The graft body portion is formed as a sleeve bellows so that the graft may be compressed or elongated slightly while retaining its generally cylindrical configuration. In addition, this graft requires longitudinal stiffeners positioned axially along the exterior cylindrical wall of the graft body for providing a length adjustment capability to and for stiffening the cylindrical wall.

Prior to insertion, a capsule band is spirally wrapped around the collapsed and compressed graft. After the graft and capsule band have been positioned at the desired location, the band is removed allowing the stiffening members to expand into place within the blood vessel. This graft also includes a tacking system wherein barbed tacks are manually inserted by the surgeon using a tacking apparatus. The tacking is accomplished by manipulating a tack into place and causing it to penetrate and travel through the body of the graft and the wall of the aorta.

Another type of intraluminal device which is expandable and can be used for dilating an intravascular stenosis is exemplified by U.S. Pat. No. 4,585,000 (Hershenson). This device employs an expandable pressure applying assembly having a nut which is attached to a sinuous threaded rod. By applying a rotational force to the rod, the surgeon expands the assembly by urging the threaded rod through the nut, causing the assembly to expand and to bear against the walls of the surrounding vessel. The threaded-rod-and-nut assembly can be difficult to manufacture and be subject to thread-jamming or thread-stripping. Also, the operative rotational force must be applied to the length of the threaded rod and the force can be reduced or unpredictable due to the dissipation of the force over the rotated length of the rod.

Other types of intraluminal grafts employ wire mesh tubes into which a deflated balloon catheter is inserted, as in U.S. Pat. Nos. 4,733,665, 4,739,762, and 4,776,337, all to Palmaz. Once the graft is put into position, the balloon is expanded, thereby axially expanding the wire mesh tube to the desired intraluminal diameter. Such tubes, however, have a rigid architecture which may not be compliant with the actual topography of the blood vessel lumen. Insufficient expansion, or non-conforming contact with the blood vessel wall at the extrema of the graft, can permit blood leakage and further expansion of the aneurysm. On the other hand, overextension of the tube can induce the dissection of healthy sections of the blood vessel, potentially causing an iatrogenic, life-threatening emergency requiring immediate open-abdominal repair of the aorta.

Yet other types of prosthetic grafts use a combination of expandable wire mesh tubes, and the like, with an essentially cylindrical sleeve of implantable material. For these prostheses, the sleeve is pre-stretched and sutured onto expanding frames, or stents, by the surgeon before the procedure begins and placed onto a balloon-type catheter. The sleeve is collapsed to the extent possible and packaged with the stents and balloon catheter into an introduction catheter. Due to the size of the catheter, a large arterial cut-down is usually required to permit insertion of the entire assembly into the patient. Often, a cut-down management team is used to prepare and monitor the cut-down site. Due to the potential for a substantial amount of blood loss, a blood management team is also used during the procedure.

With the insertion site prepared, the surgeon inserts the introduction catheter retrogradely, typically over a guide wire, from a femoral artery into the aorta. Once the stents of the prosthesis are aligned with the proximal and distal necks of the aneurysm, the introducer catheter is retracted, the balloon catheter is inflated as necessary and the stent-graft device is emplaced across the aneurysmal sac. Tacks or other fixation devices may be used to improve the attachment of the graft to the blood vessel wall. Similar to wire mesh tubes alone, these grafts can have failures resulting from improper or non-uniform deployment within the lumen of the aorta. In addition, failures also can arise from suture failures along the frame, wire tube- or tack-induced sleeve failure, and other mechanical failures.

Current intraluminal AAA prostheses, although deliverable with a catheter, typically require the use of relatively inflexible, large-diameter catheters which themselves can add to the invasiveness of the procedure, can require the presence of additional medical staff solely for the purposes of cut-down site and blood loss management, and can increase the risk, duration, and cost of the procedure. The use of large-diameter catheters also can increase the trauma to, and amount of blood lost from the blood vessels on the catheterization route, as well as trauma to the insertion site, which may lead to a host of complications including limb ischemia by thromboembolism and infection.

Vascular endoluminal defects other than aneurysms can include arteriovenous malformations; occlusive states of the coronary, central, and peripheral vessels due to emboli, atherosclerotic plaques, and foreign matter; and arterial and venous stenosis. Non-vascular endoluminal diseases are likewise diverse and can include, for example, tracheal, esophageal, intestinal, urethral, gastric, and salpingian mural and parietal (collectively mural) defects; hypertrophic conditions such as benign prostatic hypertrophy; and occlusive conditions such as renal, urinary, and biliary calculi. In general, mural defects can include occlusions, dissections, erosions, stenoses, fistulae, ectasiae, diverticula, and the like.

As with AAA, standard surgical procedures can impose substantial trauma and risk upon the patient and, therefore, may be unavailable to those too frail or otherwise compromised to undergo a standard surgical intervention. Indeed, in some instances, the location or configuration of the endoluminal defect may preclude the use of standard surgical procedures, leaving the surgeon without an effective intervention and the patient without palliative, if not curative, relief from disease.

Minimal access surgery, including intraluminal approaches, has been advanced to decrease the trauma of surgical access without limiting exposure of the operative field. Advantages to minimal access surgery include decrease in wound complications and infections, with a corresponding accelerated recovery and convalescence. Other benefits may include decreased incidence of postoperative pneumonia, deep vein thrombosis, and adhesion formation. Furthermore, the length of hospital stay and hospital expenses can be decreased, and the patient's return to normal activity can be hastened.

There is need for an intraluminal graft and insertion device that can be delivered by a catheter which is smaller in diameter than the selected vessel, is highly conformable to the potentially irregular topography of the vessel lumen, and is implantable in the human body.

SUMMARY OF THE INVENTION

The invention herein provides an intraluminal graft, an insertion device for deploying the graft, and a method for deploying the graft in a lumen. The intraluminal graft includes a generally tubular, biocompatible body and multiple anchors attached to the interior surface of the body with barbs extending beyond the distal end of the body for penetrating a lumen wall. A self-expanding stent is positioned adjacent to the interior surface of the body. The self-expanding stent can be an engine having an engine coil. One end of the engine coil is attached to the body, and the other end of the engine coil is sized and configured for attachment to an insertion device. It is preferred that the engine include an engine lock and an engine fastener. The engine fastener can movably fasten the engine lock to the other end of the engine coil. In addition, the engine lock is preferred to be adapted to lockingly receive an end of the main anchor.

It is further preferred that the engine coil includes multiple spaced apart tabs that are biased towards the longitudinal axis of the engine coil, with each of tabs being positioned to retain one portion of the engine coil in a preselected alignment with another portion of the engine coil. Also, the engine coil can be a preselected diameter when deployed, such as between about 20 millimeters and about 35 millimeters. In general, the engine coil is adapted to exert a selectable radial force upon the interior surface of the graft body. It is also preferred that one of the anchors is a main anchor that is attached to the interior surface of the graft body. Each of the anchors can have multiple, barbed tines thereon. One embodiment of the tines includes a saw-tooth configuration. It is preferred that at least a portion of the graft body be furcated, thereby forming a distal tube and multiple proximal tubes. It is also preferred that at least one of the proximal tubes have a loop attached thereto, the loop being suitable for snaring and manipulation thereof.

The insertion device for introducing the intraluminal graft in a lumen includes a deployment catheter and a deployment grip attached thereto. The deployment catheter is preferred to include a deployment shaft and an expanding frame. It is preferred that the expanding frame be movably attached to the distal end of the deployment shaft and be suitable for radially expanding an intraluminal graft. The expanding frame is preferred to have multiple arms forming an umbrella-like assembly, with each of the plurality of arms having a central end and a peripheral end. The central end of each of the arms is slidably attached to and radially disposed around the deployment shaft. The peripheral end of each of the arms is adapted for expanding the intraluminal graft.

Furthermore, the expanding frame is preferred to include a frame guide connected to the peripheral end of each of the plurality of arms, and having a plurality of struts generally aligned axially relative to the deployment shaft.

The insertion device can include an engine for radially expanding the expanding frame, and a feed shaft generally parallel to the deployment shaft. In general, the feed shaft is adapted to move generally parallel relative to the deployment shaft and to advance the engine therealong. A deployment grip is connected to the proximal end of the deployment shaft and reversibly operates the expanding frame by urging a catheter coil connected between the umbrella-like assembly of the expanding frame and the deployment grip.

To facilitate deployment of the intraluminal graft, it is preferred in one embodiment of the invention herein that the deployment grip have a hollow grip body, a sheath coupler, a track grip, and a graft deploy grip. The grip body can have first, second, and third ports. The sheath coupler is connected between the third port and the outer sheath, with the feed track and the deployment shaft passing therethrough to first and second ports, respectively. The track grip is connected to the first port, with the feed track being connected to the track grip. The graft deploy grip is connected to the second port, and is attached to the deployment shaft. It is preferred that a check valve be disposed within the first port, so that fluid flow through the first port can be reduced substantially. In one embodiment, it is preferred that the check valve be a duckbill valve. To facilitate accurate deployment of the intraluminal graft, it is preferred that the graft deploy grip be adapted to incrementally deploy the intraluminal graft.

It is preferred that the insertion device also have an introducer sealably connected to the deployment grip to control the loss of fluid, such as blood, from the insertion site. The insertion device can also have a sheath adapted to surround at least a portion of the deployment catheter, with the outer sheath being a conduit for advancing the deployment catheter to the preselected location. It is further preferred that the deployment catheter be collapsible for removal from the vessel lumen after the intraluminal graft has been introduced therein.

The method for deploying an intraluminal graft, according to the invention herein, includes obtaining an intraluminal access site, advancing a guide wire through the intraluminal access site to a preselected location in a vessel near the endoluminal defect, advancing the outer sheath over the guide wire to the preselected intraluminal location, removing the guide wire, introducing the deployment catheter with the intraluminal graft thereon through the intraluminal access site, advancing the deployment catheter with the intraluminal graft thereon to the preselected intraluminal location, retracting the outer sheath by a preselected distance so that the intraluminal graft is exposed, expanding the expanding frame of the deployment catheter thereby expanding the intraluminal graft to a preselected diameter, affixing the graft anchors to the vessel wall, collapsing the expanding frame and withdrawing the deployment catheter from the vessel lumen. Where the intraluminal graft has a proximal loop, the method can include introducing an access catheter to a second intraluminal site, and releasably capturing the proximal loop and drawing the proximal loop into a second vessel lumen.

BRIEF DESCRIPTION OF THE DRAWINGS

FIG. 5 is a side view of the general configuration of a deployment catheter according to the invention herein.

FIG. 6a is a side view partially in section of the distal end of the deployment catheter in a stowed condition.

FIG. 7a is an end view of the distal end of the deployment catheter in a stowed condition.

FIG. 7b is an end view of the distal end of the deployment catheter in a deployed condition.

FIG. 10b is a side view partially in section of the distal end of the intraluminal dilation device in a deployed condition.

DETAILED DESCRIPTION OF THE PREFERRED EMBODIMENTS

The invention herein includes an implantable intraluminal graft, a deployment catheter for delivering the graft to a desired location in a vessel lumen, and a deployment grip for manipulating the graft and catheter to the desired location, deploying the graft, managing fluid loss, including blood, and facilitating the removal of the catheter.

Figure 1:
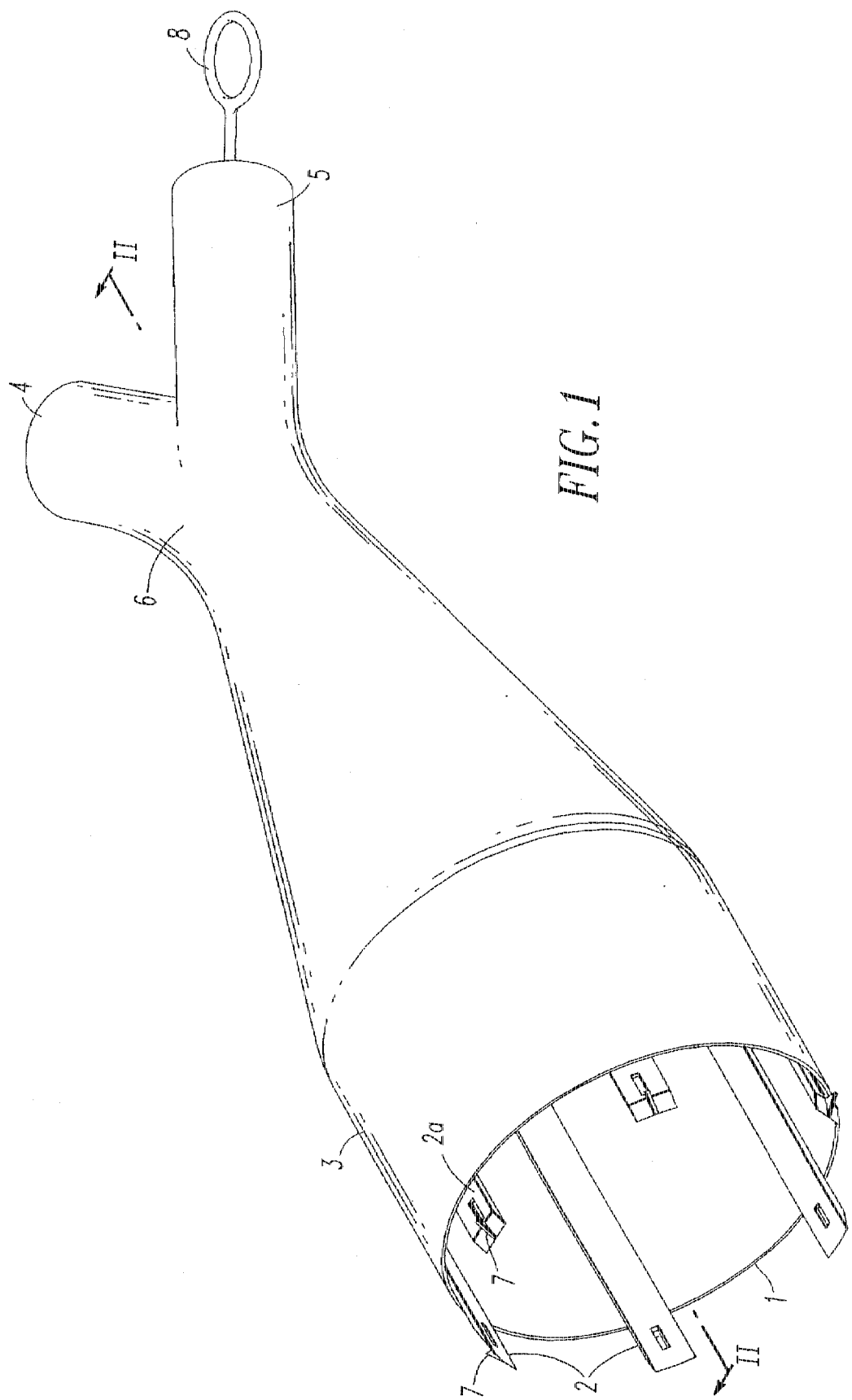
FIG. 1 is a perspective view of a present preferred embodiment of the intraluminal graft according to the invention herein.

FIG. 1 illustrates graft 1 having a plurality of anchors 2 attached thereto. Graft 1 has a generally tubular body which can be, for example, cylindrical, frusto-conical, infundibular, or asymmetric in form. Graft 1 also may have a diameter that is non-uniform and varying along its longitudinal axis, thereby permitting graft 1 to conform to a lumen or cavity having a complex or irregular topology, for example, an esophagus, trachea, or an arteriovenous malformation. In one presently preferred embodiment, at least a portion of graft 1 can be furcated so that graft 1 has a distal tube 3 and two or more proximal tubes 4, 5. Where graft 1 is used to repair abdominal aortic aneurysms, a bifurcated graft, such as graft 1, may be used with distal tube 3 being positioned proximate to the renal arteries and proximal tubes 4, 5 being positioned in the right and left common iliac arteries, respectively. In this presently preferred embodiment, graft bifurcation 6 is intended to coincide with the aortic bifurcation. Anchors 2 are preferred to be attached to the interior surface of graft 1, with the anchor barbs extending beyond the distal end of the graft body.

It is preferred that anchors 2 be evenly set apart on graft 1 so that forces upon the anchors may be evenly distributed. In the present embodiment, it is preferred that six anchors be used, with each anchor 2 being radially disposed 60° from a neighboring anchor. It is also preferred that each anchor 2 have a plurality of barbed tines 7 located at the distal end of each anchor. thereon for penetrating and becoming affixed to a vessel wall, thereby securely fastening graft 1 to the vessel. The barbed tines can be saw-toothed in shape with the perpendicular edge of a tine being proximal to the blood flow after deployment. In this way, the tine can act as a stop or resistive surface, which can keep the graft 1 from migrating with the blood flow when seated within the artery wall. At least one of anchors 2 is preferred to be a main anchor which, in FIG. 1, is anchor 2a. In addition to being attached to the interior surface of graft 1, anchor 2 is suitable for attachment at its distal end to a graft insertion device. It is further preferred that anchors 2 be attached to graft 1 during manufacture to relieve medical personnel from the burden of attaching the anchors in the preparation for the graft procedure, as is the current practice. To facilitate placement of the graft at least one proximal tube 5 has a loop 8 attached thereto for snaring from a second cut-down site and manipulation into a blood vessel distal to the aneurysm such as, for example, the common iliac artery.

Because graft 1 is intended to be a generally permanent implant within the body, it is preferred that graft 1 be made of a biocompatible material such as, for example, silk, dacron, and polytetrafluoroethylene, although in the present embodiment, polytetrafluoroethylene is particularly preferred.

To provide the force needed to urge graft 1 to securely contact the vessel inner walls, graft 1 also is preferred to have a self-expanding stent in contact with the graft interior surface. The stent can be engine coil, which engine coil is obscured in FIG. 1 but is displayed in FIG. 2.

Figure 2:
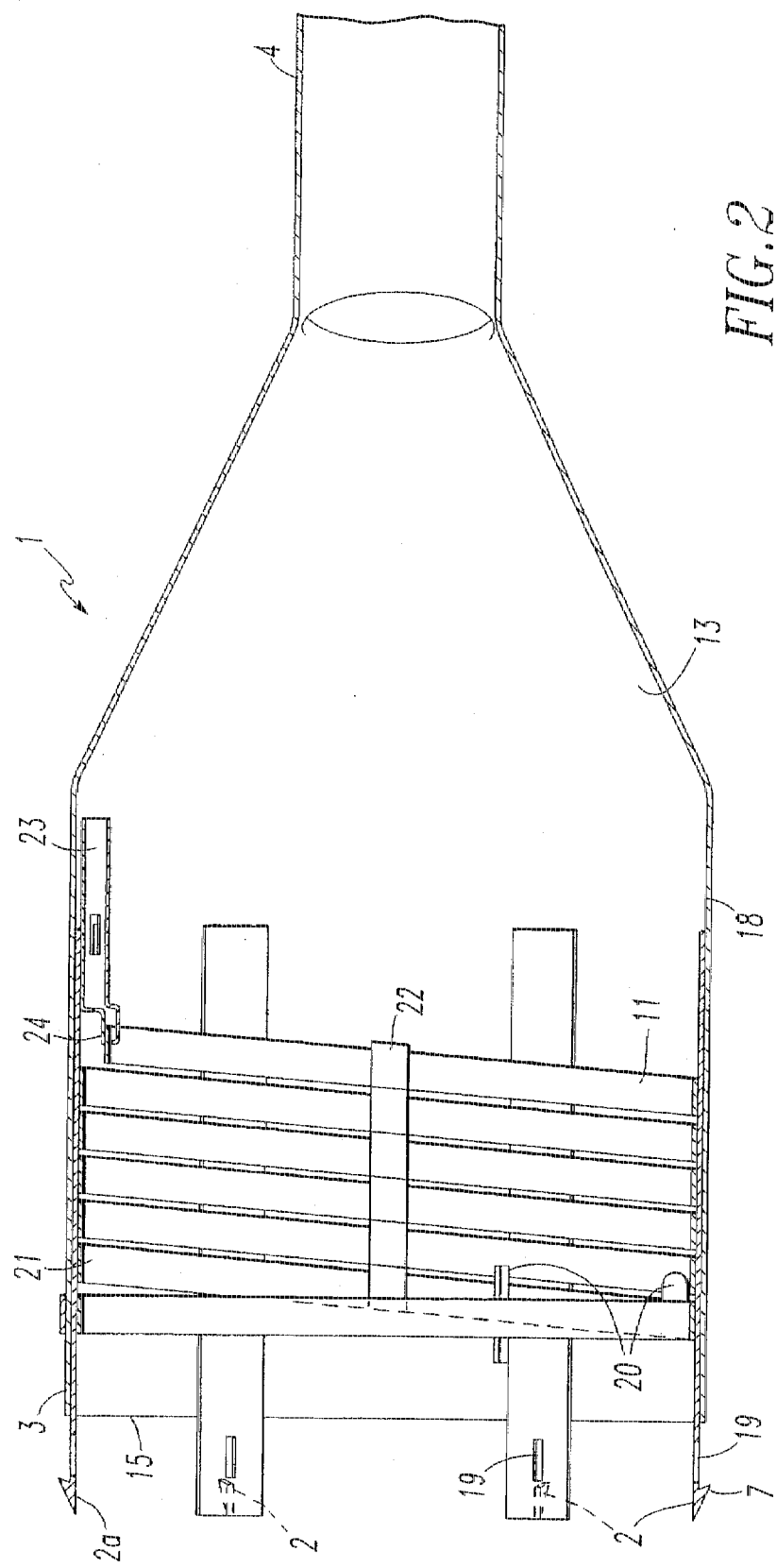
FIG. 2 is a side view partially in section taken along line II—II of FIG. 1.

As shown in the longitudinal cross-section of FIG. 2, graft 1 has engine coil 11 disposed within distal tube 3, and generally in contact with the interior surface 13 of tube 3. In general, graft 1 is disposed upon and seats with the anchors 2. In the sectional view of FIG. 2 only one proximal tube 4 is shown. Distributed around distal opening 15 of tube 3 are a plurality of spaced apart anchors 2, each having a plurality of barbed tines 7, for penetrating a vessel wall. Anchors 2 typically are attached to the interior surface 13 of tube 3. Each of anchors 2 can have a window therein, which are indicated by windows 19 in anchors 2 for connection to a deployment catheter. Anchors 2 each can have at least one engine stop 20, configured to retain distal end 21 of engine coil 11 within the body of graft 1.

In addition, engine coil 11 can have a plurality of spaced apart tabs 22 that are positioned to retain one portion of engine coil 11 in a preselected alignment with another portion of engine coil 11, so that one loop of coil 11 generally nests within the proximally subsequent loop of coil 11. To this end, it is preferred that each of tabs 22 be biased towards the longitudinal axis of graft 1. Engine coil 11 is also preferred to have an engine lock 23, which is attached to the proximal end of engine coil 11 with engine fastener 24. Engine lock 23 is adapted to lockingly receive the proximal end of main anchor 2a. Before deployment, engine coil 11 is configured as a generally elongated single helix; upon deployment, the proximal end of coil 11 is urged toward the distal end of coil 11 so that individual loops draw nearer to the preceding loops and expand radially with lock 23 engaging main anchor 2a. Coil 11 is preferred to be made of a semi-rigid material having a shape-memory function, for example, a nickel-titanium alloy wire. One such alloy wire is Nitinol wire manufactured by Nitinol Devices and Components, Inc., Fremont, Calif. The graft implants are sized according to the vessel as determined by fluoroscopy so that when the engine is locked, it exerts a selectable radial force upon the interior surface of the graft and, therefore, the wall of the vessel. Additionally, engine coil 11 can have a preselected diameter when deployed, apropos the intended application. For example, when engine coil 11 is used in an application such as an abdominal aortic aneurysm repair, the preselected diameter can be between about 20 millimeters and about 35 millimeters, which diameter is congruent with the expected range of diameters for the aorta in the abdomen. For use in other applications, it may be desirable to provide engine coil 11 with a larger or smaller preselected diameter, corresponding to the diameter of the lumen.

Figure 3:
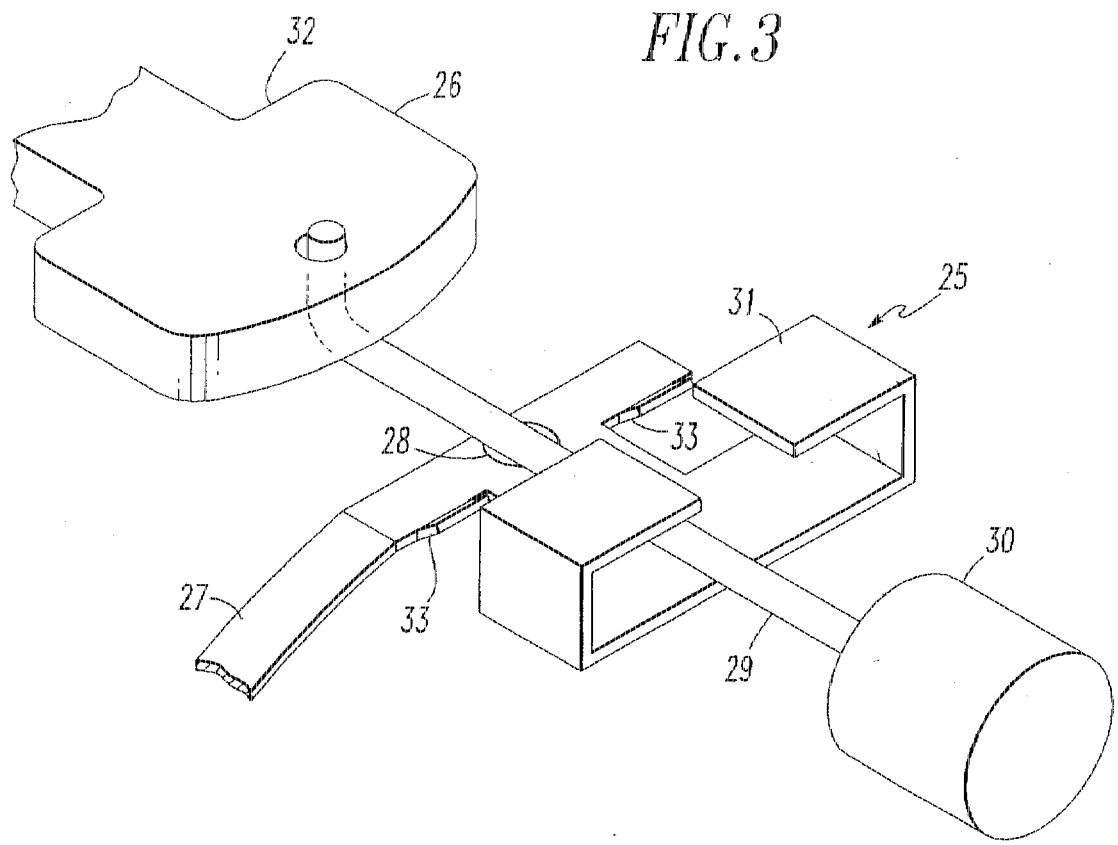
FIG. 3 is an illustration of an enlarged perspective of one embodiment of an engine lock used with the graft of FIGS. 1 and 2.

FIG. 3 provides an enlarged view of one embodiment of engine lock 25, as it is intended to mate with main anchor 26. Lock 25 is movably fastened to engine coil 27 by engine fastener 28, which can be a rivet. In general, anchor 26 can be stabilized with respect to feed track 29 such that lock 25 can be advanced by engine lock driver 30 along track 29 to come into contact with anchor 26. Upon the application of a force by the surgeon upon engine lock driver 30, locking tab 33 of lock 25 advances under anchor flange 26 until locking tab 33 mates with anchor flange 32, thereby locking engine coil 27 in the deployed position.

Figure 4:
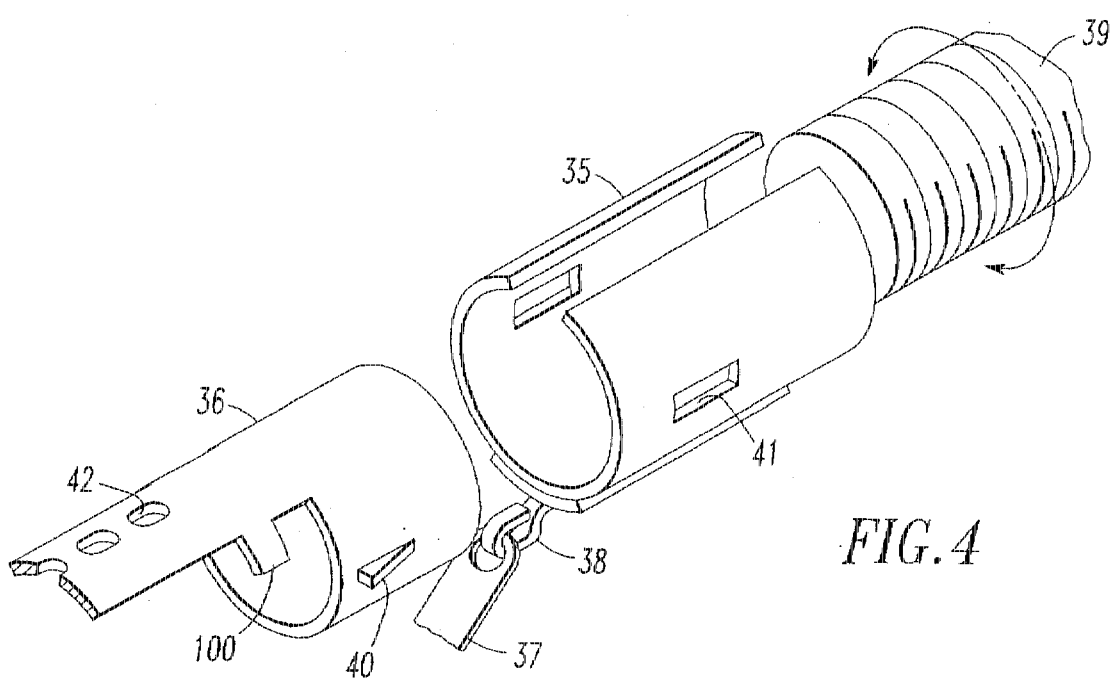
FIG. 4 is an exploded enlarged perspective of a second embodiment of an engine lock.

FIG. 4 provides an enlarged view of another embodiment of engine lock 35 as it is intended to mate with the proximal end of main anchor 36. Similar to the engine lock 25 in FIG. 3, lock 35 is movably fastened to engine coil 37 by engine fastener 38, which can be a pivot loop. Alternatively, fastener 38 can be a rivet. In general, main anchor 36 can be removably attached to feed track 39, for example, by a mating threaded-screw arrangement. In operation, engine lock 35 is advanced toward main anchor 36 using feed track 39. Engine lock 35 is guided over main anchor 36, with the application of a force by the surgeon. Locking ears 40 on anchor 36 are lockingly received into the lock windows 41 on engine lock 35. Stops 100 keep the engine lock from being advanced past the locking ears 40. A plurality of apertures 42 are provided in each anchor, for example anchor 36, to facilitate attachment of a portion of the intraluminal graft thereto.

FIG. 5 shows the general configuration of deployment catheter 45 having deployment shaft 46, an expanding frame 47 movably attached to distal end 48 of shaft 46, and a deployment grip 49, attached to proximal end 50 of shaft 46. Shaft 46 can be provided in a continuous length convenient for use by the surgeon, for example 100 cm. A portion of the engine coil can be seen on distal end 48 as a single-helix band 51 attached to the graft 1. To facilitate the introduction of the deployment catheter 45, outer sheath 52 can be adapted to surround at least the distal third portion of the deployment catheter 45. With outer sheath 52 being a cover for advancing the deployment catheter 45 to the preselected location, through an introducer (not shown).

Figure 6B:
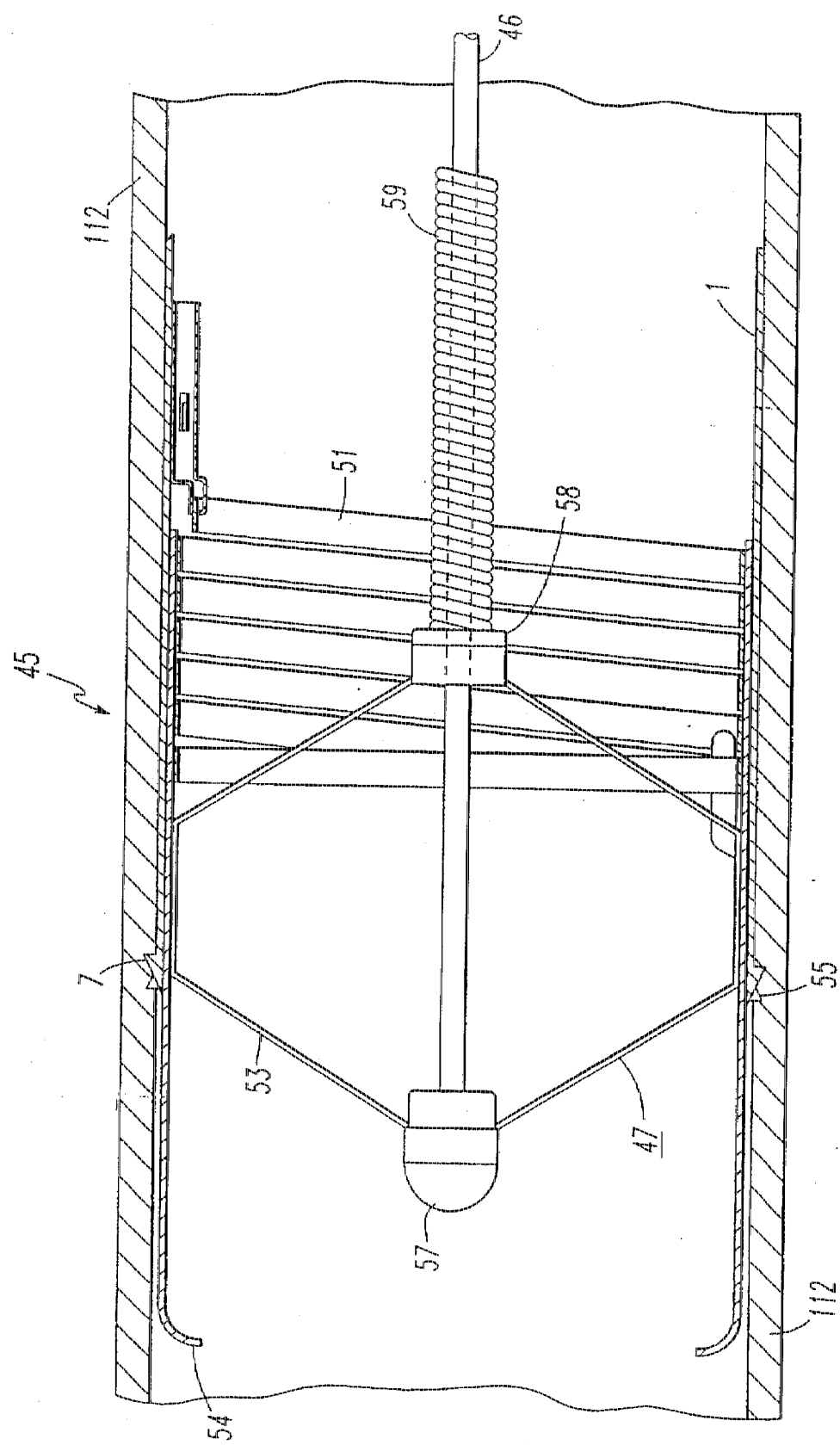
FIG. 6b is a side view partially in section of the distal end of the deployment catheter in a deployed condition.

FIGS. 6a and 6b are enlargements of distal end 48 having expanding frame 47, as shown in FIG. 5. In FIG. 6a, expanding frame 47 is shown in the stowed, or non-expanded condition. The frame is in this position before and during the insertion procedure. FIG. 6b illustrates expanding frame 47 in the deployed, or expanded, condition. The frame is moved to this position when graft 1 is in place at the aneurysm. Expanding frame 47 is suitable for radially expanding an intraluminal graft.

As seen in FIG. 6b, once the outer sheath 52 in FIG. 5 has been removed, the expanding frame 47 is deployed against the walls 112 of the aorta, thus carrying intraluminal graft 1 outward in a radial fashion. Frame 47 includes a plurality of arms 53 forming an umbrella-like assembly, with each of arms 53 being centrally attached to deployment shaft The number of arms 53 employed generally coincides with the desired number of anchors on intraluminal graft 1. At their peripheral ends, each of arms 53 are attached to expanding frame guide 54. It is preferred to provide a plurality of expanding frame hooks 55 on arms 53, with each of hooks 55 being adapted to removably mate with graft anchor windows, such as windows 19 in FIG. 2. To facilitate axial movement of frame 47 respective of deployment shaft 46, arms 53 can be centrally gathered in nose 57, which is affixed to the most distal end of shaft 46. Similarly, arms 53 can be centrally gathered in cup 58.

Along at least a portion of the length of the deployment shaft 46 is a resilient member, which is preferred to be catheter coil 59. In general, coil 59 is adapted to contact cup 58 at its distal end and the deployment grip 75 in FIG. 8. When deploying the graft, the surgeon applies a tractive force to deployment knob 85 in FIG. 8, causing the deployment shaft 46 to pull back towards the grip so that frame 47 is urged from the stowed condition to the deployed condition. Coil 59 creates a resistive force between the cup 58 and the grip 75 in FIG. 8. In general, this coil and deployment shaft assembly allows for the catheter 45 as a whole to travel through often tortuous blood vessels to the desired graft site.

FIGS. 7a and 7b show head-on views of the extreme distal portion of catheter 60, similar to catheter 45 in FIGS. 6a and 6b. FIG. 7a shows expanding frame 62 in the stowed condition in which graft 1 is shown in the packed position for delivery. FIG. 7b shows expanding frame 62 in the deployed condition. In expanding frame 62 in FIG. 7a, portions 61 of each of the plurality of frame guide struts are biased towards the center such that portions 61 at least partially cover nose 64. Main anchor 65a is at the twelve-o'clock position of plurality of anchors 65. Each of anchors 65 can have a plurality of barbed tines, such as tines 66 on anchor 65a. In the embodiment in the figure, it is preferred that expanding frame hooks 67 be positioned to fit in the anchor windows, such as window 19 in FIG. 2, that can be situated midway between the barbed tines, such as hook 67 between tines 66 on anchor 65a.

When catheter 60 is deployed within vessel lumen 68, as seen in FIG. 7b, arms of the expanding frame 69 expand radially until contact of vessel wall 70 is made by graft 1. Anchors 65 also contact wall 70, causing the barbed tines, such as tines 66 on anchor 65a, to penetrate into wall 70. Once the deployment of graft 1 has been effected, the engine is urged into position by the lock driver, such as lock driver 30 in FIG. 3, and locked in place. The track, such as track 29 in FIG. 3, is undone from the main anchor and removed with the lock driver from the grip. Arms 69 are collapsed and catheter 60 reassumes the stowed condition, as seen in FIGS. 6a and 7a.

Figure 8:
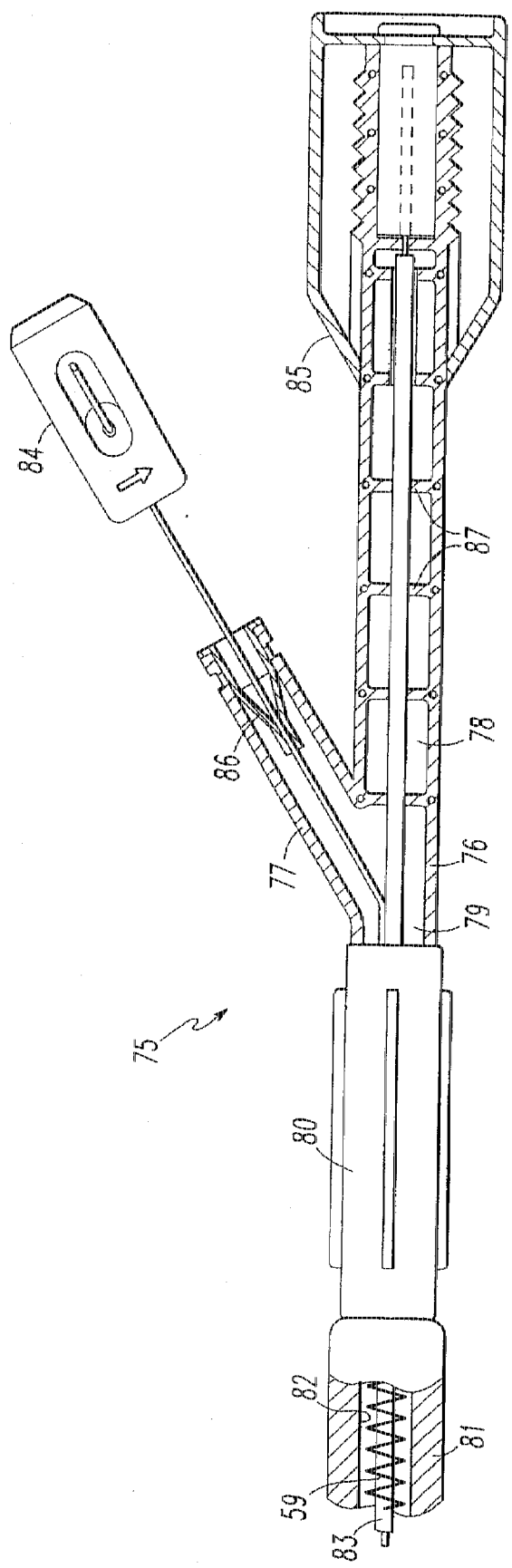
FIG. 8 is a side view partially in section of a first embodiment of a deployment grip according to the invention herein.

In the preferred embodiment in FIG. 8, deployment grip 75 has a generally hollow, Y-shaped grip body 76 having first port 77, second port 78 and third port 79. Sheath coupler 80 is connected between third port 79 and the introducer 81. Through port 79 passes feed track 82 and deployment shaft 83 as well as the coil, such as coil 59 in FIGS. 6a and 6b. Track 82 extends to first port 77 and deployment shaft 83 extends to second port 78. Track grip 84 is connected to first port 77 by a locking system, and is operably attached to feed track 82. Similarly, graft deployment knob 85 is connected to second port 78 and is operably attached to deployment shaft 83. Graft deployment knob 85 is used by the surgeon to open the expanding frame of the deployment catheter at the preselected graft location. As the expanding frame opens, the graft also opens, thus bringing the graft into contact with, and causing the graft anchors to become embedded in, the blood vessel walls. One embodiment of the graft is described in FIG. 2 and the accompanying text.

Once the anchors have been set into the blood vessel walls, the graft is considered to be deployed. The surgeon then can lock the engine coil into place by advancing the engine lock along the feed track towards the main anchor until the engine lock is lockingly engaged by the locking ears 40 on the main anchor. By manipulating deployment knob 85, the expanding frame can return to the stowed condition. As previously described with reference to FIG. 6b, the expanding frame hooks are removably mated with windows in the graft anchors and thus disengage from the graft anchors when the expanding frame is stowed, permitting frame removal without disturbing the graft attachment.

In order to control the flow of body fluids, such as blood, from the patient through the introducer 81. sheath coupler 80 locks into first port 77 and the fitting of the introducer 81, which is preferred to be a Luer fitting. Check valve 86 also can be fitted into first port 77. It is preferred that check valve 86 be a duckbill valve, as shown. To inhibit the flow of fluid through grip body 76 and port first 77, a plurality of baffles 87 are adapted to permit deployment shaft 83 therethrough, and be accepted into graft deployment knob 85.

Figure 9:
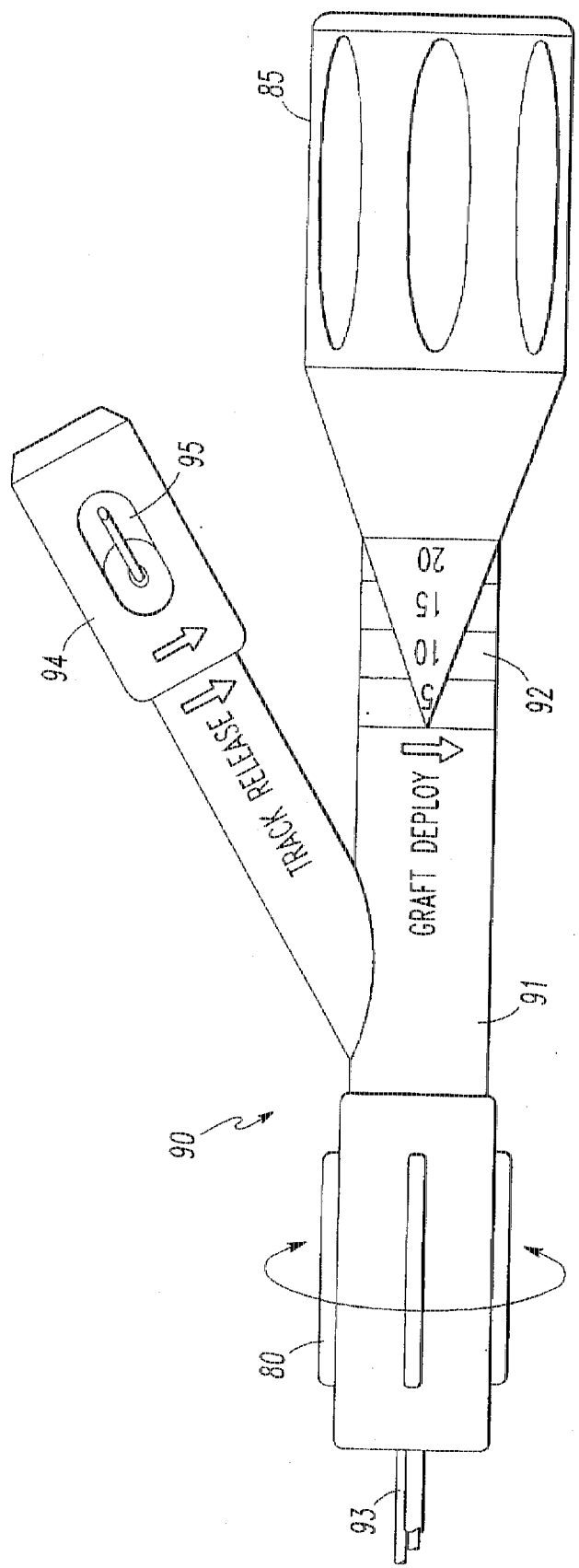
FIG. 9 is a side view of a second embodiment of a deployment grip according to the invention herein.

It is desirable to make the graft expansion diameter selectable by the surgeon. This can be accomplished by adapting graft deployment knob 85 in FIG. 9 to incrementally expand the graft diameter as the surgeon turns knob 85 in the deployment direction. Knob 85 can be attached to grip body 91 such that selectable graft deployment diameters can be indicated by graduated graft deployment scale 92. The surgeon can use scale 92 as a direct indicator of graft deployment diameter and can use scale 92 in conjunction with measurements made under fluoroscopy during the procedure. When it is desired to manipulate feed track 93, grip 94 can be rotated in a second direction, opposite the first direction, so that feed track 93 may be freely moved through grip body 91. Track attachment gate 95 can be used to secure the distal end of the engine lock driver.

The particular configuration of the graft and engine enables them to be constructed of a size that will fit through an 18 French, or smaller, sheath. Hence, the graft can be placed without exposing, incising, removing, replacing, or bypassing the defective blood vessel, thereby reducing post-surgical complications. In addition, smaller-sized catheters require smaller insertion site incisions and can be easier to manipulate through tortuous blood vessels, thereby lessening the trauma that can be associated with the procedure.

In one embodiment of the presently preferred method, where an abdominal aortic aneurysm is repaired, endovascular access is obtained by performing a cut-down procedure on a common femoral or common iliac artery. Many surgeons prefer to use the right-sided arteries, although the left-sided arteries may be used. Depending upon the size of the cut-down needed, the procedure may be performed by a surgical team or by a separate cut-down team. To manage the flow of blood released through the cut-down, an introducer may be inserted. Although the preferred introducers are not yet commercially available, that type of introducer can be created by modifying polytetrafluoroethylene tubing in 18-, 20-, 22-, or 24-French diameters to receive the graft and deployment device. Furthermore, other types of introducers may be used as indicated by the situation at hand.

Next, a guide wire can be advanced through the introducer site through the access arteries to the aorta where the guide wire is advanced across the aneurysmal sac. Next, an outer sheath can be advanced over the guide wire and into position across the aneurysmal sac. Although an 18-French sheath is presently preferred, other size sheaths may also be used. It is preferred to use the smallest size catheter possible. A 14-French sheath may also be inserted into the femoral or iliac arteries on the side opposite to the cut-down site. This catheter can be used as an access port to guide the length of the graft down the common iliac artery. With the outer sheath in place, the guide wire may be removed.

The deployment catheter with intraluminal graft can be introduced into the sheath and advanced forward to the aneurysmal site. Once in position, the protective outer sheath is removed through the introducer. The sheath coupler on the deployment grip is affixed to the end of the outer sheath by rotating the sheath coupler in the closed direction. Using fluoroscopy, the distal end of the deployment catheter is emplaced just below the renal arteries. The outer sheath can be retracted clear of the graft. The exposed intraluminal graft is then urged into position by turning the graft deploy grip.

Where the grip has a knob with an incremental deployment scale, the knob can be turned to the preselected amount of deployment by the surgeon. The size of the graft and its positioning are typically pre-established by a previous diagnostic procedure. The lock driver can be threaded into the track attachment gate in the track grip. The driver can be advanced through the valve along the track until it meets the proximal end of the engine lock. The surgeon applies a force to the driver to urge the engine lock along the track and into position as to be lockingly received by the main anchor. The track and driver can then be unscrewed by twisting the track grip. A proximal tube of the graft can be snared and pulled over to the desired artery by way of the smaller 14-French access catheter.

The deployment catheter can then be collapsed by returned the graft deploy grip to a neutral position, thus collapsing the expanding frame of the deployment catheter. The deployment catheter is then retracted through the outer sheath, and the entire assembly is removed from the patient. Using standard techniques, the cut-down site can be closed and the procedure completed. The method similarly can be employed to repair other types of endoluminal and mural defects, with the intraluminal access sites and vessels being selected accordingly.

Figure 10A:
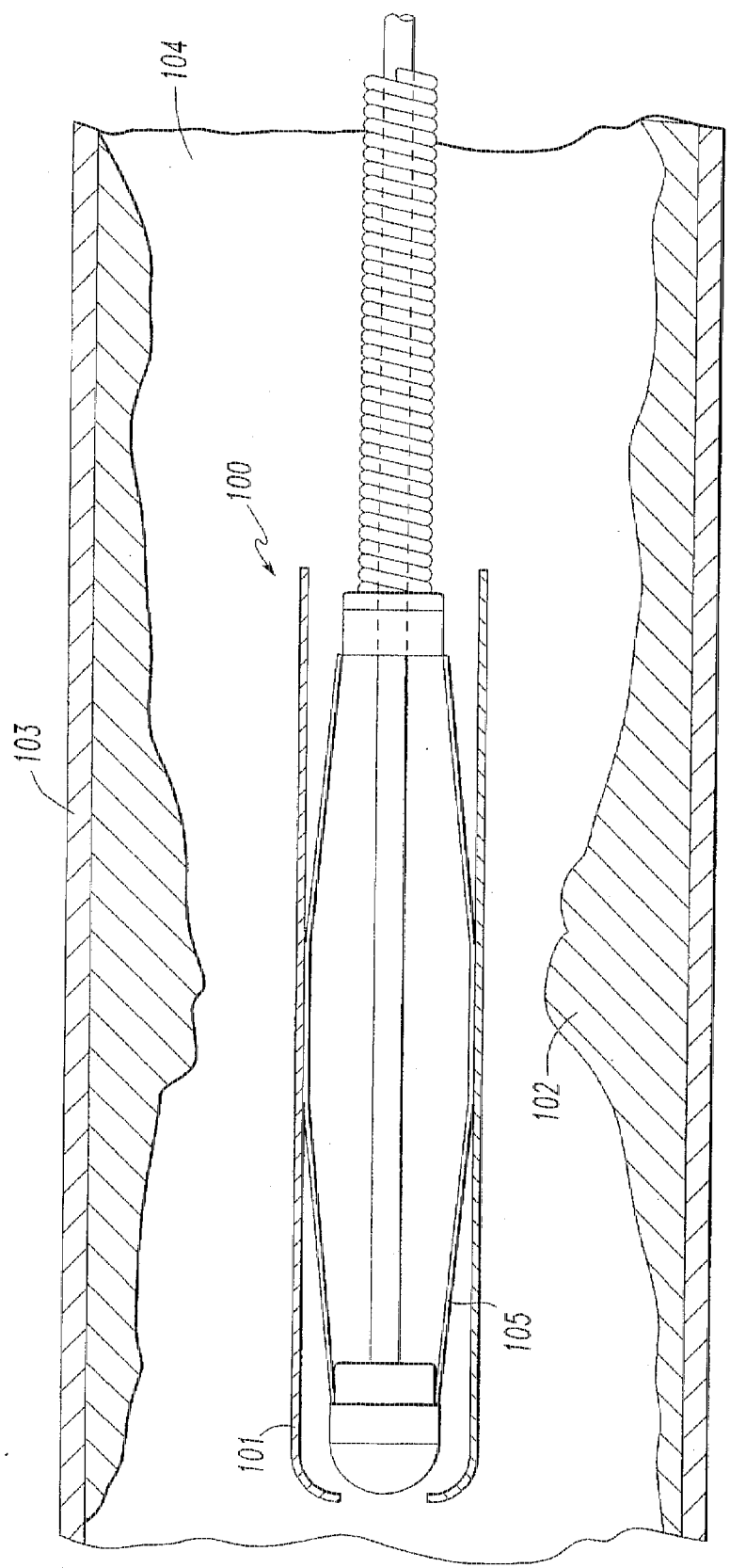
FIG. 10a is a side view partially in section of the distal end of the intraluminal dilation device in a stowed condition.
Figure 10C:
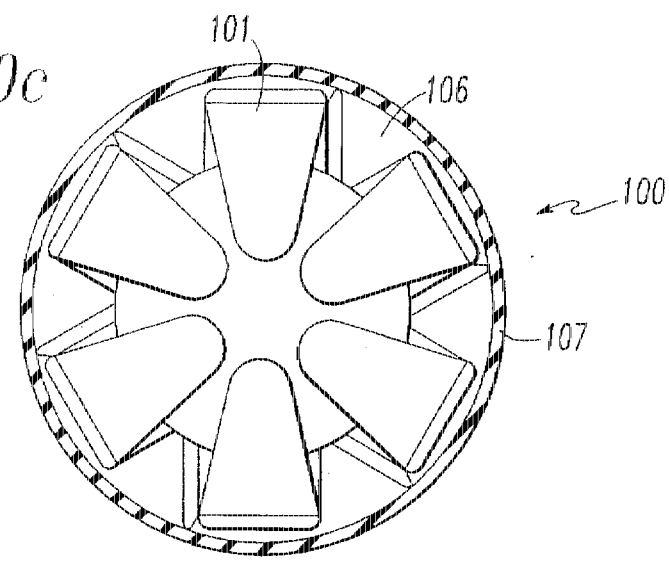
FIG. 10c is an end view of the distal end of the intraluminal dilation device in a stowed condition.

The insertion device can be used without a graft, such as graft 1 in FIG. 1, as an intraluminal dilation device to dilate restrictive endoluminal defects such as a stenosis or a partial occlusion of a lumen. FIG. 10a illustrates intraluminal dilation device distal end 100, which is similar to distal end 48 in FIGS. 5 and 6a. In this present embodiment, it is preferred that expanding frame arms 101 not have expanding frame hooks, such as frame hooks 55 in FIG. 6a. In FIG. 10a, distal end 100 is situated within an endoluminal defect, which is, for example, an accretion of atherosclerotic plaque 102 on vessel wall 103 and which partially occludes lumen 104. FIG. 10c illustrates distal end 100 in the stowed position, as in FIG. 10a, from an end-on view of the distal end. Expanding frame arms 101 can have gaps 106 therebetween and, therefore, distal end 100 can be fitted with expandable tubular covering 107 disposed therearound to bridge the gaps and to provide a generally radially-uniform dilation of lumen 104.

Using techniques similar to those discussed in conjunction with FIGS. 6a through 9, intraluminal dilation device distal end 100 is guided to the intraluminal location of plaque 102 and the expanding frame 105 is deployed. FIG. 10b illustrates the opening of expanding frame 105 such that plaque 102 is crushed against vessel wall 103 by expanding frame arms 101, thereby improving the patency of lumen 104.

Figure 11:
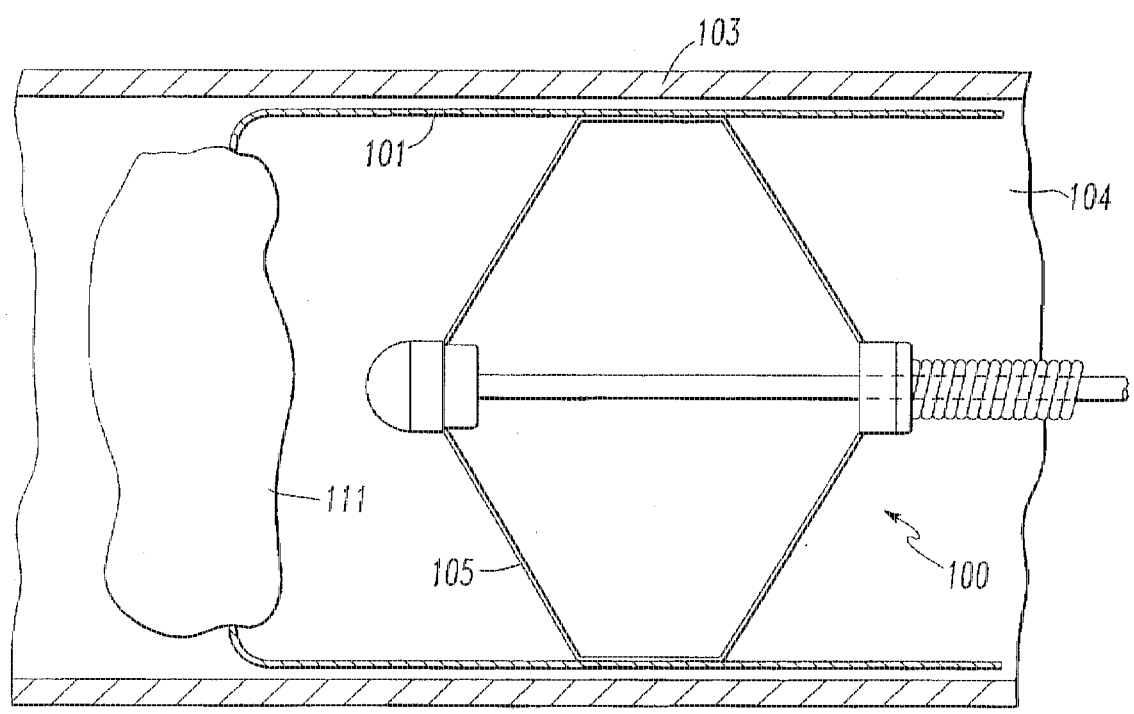
FIG. 11 is a side view partially in section of the distal end of the intraluminal dilation device in a deployed condition and engaged with an intraluminal object.

The intraluminal dilation device also can be used to remove objects which may be partially or fully occluding a vessel lumen. FIG. 11 illustrates deployed expanding frame 105 engaged with object 111 which is at least partially occluding lumen 104. Object 111 can be, for example, a thrombus, a calculus, or an atherosclerotic plaque. Expanding frame arms 101 can be expanded to dilate lumen 104 and engage object 111. When expanding frame arms 101 in distal end 100 are fully or partially collapsed, at least a portion of object 111 is retained by expanding frame arms 101, and removed with the insertion device distal end 100 from vessel lumen 104.

The preferred embodiments and methods have been described with reference to their use in blood vessels, and primarily for abdominal aortic aneurysms. Nevertheless, the apparatus for graft insertion and lumen dilation, and method for dilating a lumen, are not so limited but can be used in any generally tubular passageway. When so used, the size and shape of the apparatus likely would be somewhat different from the preferred embodiments described above.

While specific embodiments of the invention have been described in detail, it will be appreciated by those skilled in the art that various modifications and alternatives to those details could be developed in light of the overall teachings of the disclosure. Accordingly, the particular arrangements of apparatus and the particular steps of the methods disclosed are meant to be illustrative only and not limited to the scope of the invention which is to be given the full breadth of the following claims and any and all embodiments thereof.

We claim:

1. A graft delivery device for delivering a graft within a vessel lumen, the graft including a plurality of anchor struts, each one of the plurality of anchor struts having a portion defining a window, the graft delivery device comprising:

a catheter coil having a lumen, a proximal end and a distal end;

a cup member affixed to the distal end of the catheter coil, the cup member having a portion defining an aperture that is aligned with the lumen;

a deployment shaft having a proximal end, a distal end, and a longitudinal axis, the deployment shaft disposed within the lumen so that the distal end of the deployment shaft extends through the aperture and is spaced apart axially from the cup member, the proximal end extending beyond the proximal end of the catheter coil;

a nose member affixed to the distal end of the deployment shaft;

a plurality of expanding arms, each one of the plurality of expanding arms including a proximal end affixed to the cup member, a distal end affixed to the nose member, and a mid-section disposed between the proximal and distal ends and aligned parallel to the longitudinal axis, the plurality of expanding arms movable between a first position wherein the mid-sections are adjacent to the deployment shaft and a second position wherein the mid-sections are spaced radially apart from the deployment shaft;

a plurality of expandable frame guides, each one of the plurality of expandable frame guides having a first length at least as long as a distance between the nose member and the cup member when the plurality of expanding arms are in the first position, each one of the plurality of expandable frame guides affixed to a mid-section of a respective one of the plurality of expanding arms, the plurality of expandable frame guides being maintained parallel to the longitudinal axis of the deployment shaft as the plurality of expanding arms is moved between the first and second positions; and a hook disposed on each one of the plurality of expandable frame guides for engaging the window of a corresponding anchor strut, wherein, when the proximal end of the deployment shaft is retracted in a proximal direction relative to the catheter coil, the plurality of expanding arms bow radially outward to the second position and exert an outward force, the plurality of expandable frame guides distributing the outward force over a length of the vessel lumen equal to the first length.

2. The graft delivery device of claim 1 further comprising means for retracting the deployment shaft in the proximal direction in predetermined increments.

3. The graft delivery device of claim 1 wherein each one of the plurality of expandable frame guides includes a distal end that is curved radially inward.

4. The graft delivery device of claim 1 wherein the hook of each one of the plurality of expandable frame guides releasably engages the window of the corresponding anchor strut.

5. The graft delivery device of claim 1 further comprising a deployment grip, the proximal end of the catheter coil being affixed to the deployment grip.

6. The graft delivery device of claim 5 wherein the means for retracting the deployment shaft in the proximal direction in predetermined increments further comprises a plurality of baffles that reduce the flow of fluid through the deployment grip.

7. The graft delivery device of claim 1 wherein the graft is deployed when the plurality of expanding arms is moved to the second position.

8. The graft delivery system of claim 1 wherein the plurality of expanding arms comprises six expanding arms spaced equidistant circumferentially around the deployment shaft.

9. Apparatus for dilating a vessel lumen comprising:

a catheter coil having a lumen, a proximal end and a distal end;

a cup member affixed to the distal end of the catheter coil, the cup member having a portion defining an aperture that is aligned with the lumen;

a deployment shaft having a proximal end, a distal end, and a longitudinal axis, the deployment shaft disposed within the lumen so that the distal end of the deployment shaft extends through the aperture and is spaced apart axially from the cup member, the proximal end extending beyond the proximal end of the catheter coil;

a nose member affixed to the distal end of the deployment shaft;

a plurality of expanding arms, each one of the plurality of expanding arms including a proximal end affixed to the cup member, a distal end affixed to the nose member, and a mid-section disposed between the proximal and distal ends and aligned parallel to the longitudinal axis, the plurality of expanding arms movable between a first position wherein the mid-sections are adjacent to the deployment shaft and a second position wherein the mid-sections are spaced radially apart from the deployment shaft;

a plurality of expandable frame guides, each one of the plurality of expandable frame guides having a first length at least as long as a distance between the nose member and the cup member when the plurality of expanding arms are in the first position, each one of the plurality of expandable frame guides affixed to a mid-section of a respective one of the plurality of expanding arms, the plurality of expandable frame guides being maintained parallel to the longitudinal axis of the deployment shaft as the plurality of expanding arms is moved between the first and second positions, wherein, when the proximal end of the deployment shaft is retracted in a proximal direction relative to the catheter coil, the plurality of expanding arms bow radially outward to the second position and exert an outward force, the expandable frame guides distributing the outward force over a longitudinal distance equal to the first length.

10. The apparatus of claim 9 further comprising means for retracting the deployment shaft in the proximal direction in predetermined increments.

11. The apparatus of claim 10 wherein the means for retracting the deployment shaft in the proximal direction in predetermined increments further comprises a plurality of baffles that reduce the flow of fluid through the deployment grip.

12. The apparatus of claim 9 wherein each one of the expandable frame guides includes a distal end that is curved radially inward.

13. The apparatus of claim 9 further comprising an expandable tubular cover disposed over the plurality of expandable frame guides, the expandable tubular cover radially distributing the outward force.

14. The apparatus of claim 9 further comprising a deployment grip, the proximal end of the catheter coil affixed to the deployment grip.

15. The apparatus of claim 9 wherein the plurality of expanding arms comprises six expanding arms spaced equidistant circumferentially around the deployment shaft.

16. A method for dilating a vessel lumen with an intraluminal dilation device, comprising steps of:

providing an intraluminal dilation device comprising a catheter coil having a lumen, a deployment shaft disposed within the lumen and arranged for reciprocation therethrough, a plurality of expanding arms, each one of the plurality of expanding arms having a first length, a proximal end coupled to the catheter coil, a distal end coupled to the deployment shaft, and a mid-section aligned parallel to a longitudinal axis of the deployment shaft, the plurality of expanding arms movable between a first position wherein the plurality of expanding arms are adjacent to the deployment shaft and a second position wherein the expanding arms bow radially outward and exert an outward force, and a plurality of expandable frame guides, each one of the plurality of expandable frame guides affixed to a corresponding one of the plurality of expanding arms and having a second length at least as long as the first length;

creating an intraluminal access site;

advancing a guide wire through the intraluminal access site to a predetermined location in the vessel lumen;

introducing the intraluminal dilation device through the access site; and retracting the deployment shaft in a proximal direction relative to the catheter coil to move the plurality of expanding arms to the second position, so that the plurality of expandable frame guides distributes the outward force over a length of the vessel lumen equal to the second length.

17. The method of claim 16 wherein the step of providing an intraluminal dilation device further comprises a step of providing an expandable tubular cover disposed over the plurality of expandable frame guides, the step of retracting the deployment shaft further comprising a step of distributing the outward force radially within the vessel lumen.

18. The method of claim 16 wherein the step of retracting the deployment shaft comprises a step of retracting the deployment shaft in predetermined increments.

* * * * *